United States Patent [19]

Kuroyanagi et al.

[11] Patent Number: 5,523,692
[45] Date of Patent: Jun. 4, 1996

[54] OIL DETERIORATION DETECTOR

[75] Inventors: Susumu Kuroyanagi, Anjo; Tetsuo Fujii, Toyohashi; Kingo Okada, Kariya; Masaei Nozawa, Okazaki; Syuji Yamaguchi, Toyokawa; Kiwamu Naito, Kariya, all of Japan

[73] Assignee: Nippondenso Co., Ltd., Aichi, Japan

[21] Appl. No.: 215,759

[22] Filed: Mar. 22, 1994

[30] Foreign Application Priority Data

| Mar. 23, 1993 | [JP] | Japan | 5-088052 |
| Mar. 25, 1993 | [JP] | Japan | 5-092228 |
| Jun. 30, 1993 | [JP] | Japan | 5-160903 |
| Sep. 8, 1993 | [JP] | Japan | 5-223505 |

[51] Int. Cl.$^6$ .................................................. G01R 27/08
[52] U.S. Cl. ........................ 324/438; 324/698; 340/438
[58] Field of Search .................................. 324/438, 439, 324/444, 698, 722, 724; 340/438, 603; 73/53.05, 61.44; 204/421

[56] References Cited

U.S. PATENT DOCUMENTS

| 4,701,713 | 10/1987 | Eaton et al. | 324/439 |
| 5,089,780 | 2/1992 | Megerle | 324/698 |
| 5,146,169 | 9/1992 | Morishita et al. | 324/438 |
| 5,331,287 | 7/1994 | Yamagishi et al. | 324/724 |

FOREIGN PATENT DOCUMENTS

| 0442314 | 8/1991 | European Pat. Off. |
| 61-20851 | 1/1986 | Japan . |
| 62-25250 | 2/1987 | Japan . |
| 3175350 | 7/1991 | Japan . |
| 462336 | 10/1992 | Japan . |
| 4350552 | 12/1992 | Japan . |
| 55720 | 1/1993 | Japan . |

OTHER PUBLICATIONS

Daniel J. Soltz, "High MOS Impedance Benefits pH Measurement", Jul. 1966, Electronics (TK7800.E58), p. 79.

"Oil–Degradation Monitors—GM Could Be First"; The Hansen Report on Tutomotive Electronis; A Business and Technology Newsletter; vol. 6, No. 6; Jul./Aug. 1993.

Hirosawa et al:, "Development of Deterioration Sensor for Engine Oil", Japanese Automobile Article 921, 1992-5, pp., 123–126 month unavailable.

Fog et al:. "Electronic Semiconducting Oxides as $_pH$ Sensors", Sensors and Actuators, 5(1984), pp. 137–146 month unavailable.

Kinoshita et al: "Electrochemical Measurements on Pt, Ir, and Ti Oxides as $_pH$ Probes"; Electrochem. Soc.: Electrochemical Science And Technology; May, 1984, pp. 1089–1094.

Primary Examiner—Kenneth A. Wieder
Assistant Examiner—Christopher M. Tobin
Attorney, Agent, or Firm—Cushman Darby & Cushman

[57] ABSTRACT

An oil deterioration detector comprising a sensitive electrode whose electric potential varies in response to acidity and/or basicity of oil to be measured, and a reference electrode associated with this sensitive electrode. An electrically conductive housing accommodates the sensitive electrode and the reference electrode together with the oil. A potential difference detector detects oil deterioration by measuring a potential difference between the sensitive electrode and the reference electrode. And, an insulating member is interposed between these electrodes and the electrically conductive housing for electrically insulating these electrodes from the electrically conductive housing. The reference electrode is grounded together with the electrically conductive housing. An insulating, hydrophilic porous member would be interposed between the sensitive electrode and the reference electrode.

19 Claims, 14 Drawing Sheets

1

OIL DETERIORATION DETECTOR

BACKGROUND OF THE INVENTION

1. Field of the Invention

The present invention relates to an oil deterioration detector which detects deterioration of oil by detecting acidity and/or basicity of oil.

2. Description of the Related Arts

One of conventional methods for detecting deterioration of oil is to measure a potential difference between a reference electrode and a sensitive electrode which are made of different metals, as disclosed in Unexamined Japanese Patent Application No. HEI 3-175350/1991 and Japanese Patent No. HEI 4-62336/1992.

For example, the former discloses a reference electrode made of base metal, such as lead, and a sensitive electrode made of electrically conductive solid material, such as stainless steel having an oxide membrane thereon. Measuring a potential difference between these reference electrode and sensitive electrodes, acidity and/or basicity (hereinafter pH) of oil is detected.

It is estimated, in this related art, that the electric potential of the reference electrode is stable even if the pH value of oil varies, because the base metal such as lead, when used as the reference electrode, mainly causes electrolytic dissolution into the oil. On the contrary, the electric potential of the sensitive electrode, which is made of electrically conductive solid electrode, tends to vary depending on the equilibrium between OH ions absorbed on the electrode surface and H ions representing the pH value of the oil. Furthermore, it is also estimated that the electric potential is stabilized when an oxide membrane is formed on the electrically conductive solid electrode.

In the case where above-described electrodes are incorporated into an oil deterioration detector for an automotive vehicle, these paired electrodes need to be put or dipped into an oil circulating circuit. However, the oil circulating circuit is normally constituted by numerous oil devices made of metal (e.g. carbon steel), such as a pump, an oil filter, an oil cooler, an oil tank, and piping. It means that, from the view point of electrochemistry, these metallic oil devices can perform as one of electrodes. In other words, a total of three electrodes is put or dipped into the oil.

Accordingly, a potential difference is caused between the metallic oil devices and the metallic electrode (reference electrode); thus, a significant amount of electric current flows between the metallic oil devices and the reference electrode. In the same manner, a potential difference is caused between the metallic oil devices and the electrically conductive solid electrode (sensitive electrode); thus, a significant amount of electric current flows between the metallic oil devices and the electrically conductive solid electrode. This phenomenon adversely affects the signal voltage to be detected between the reference electrode and the electrically conductive solid electrode. Especially, to detect a potential difference between these electrodes, this technology requires a potentiometer with an internal resistance (input impedance) of approximately $10^{11}$ which is an extremely high resistance. Hence, if the metallic oil devices—third electrode (earth electrode)—are disposed close to the metallic electrode and/or the electrically conductive solid electrode, it will incur the serious decline of S/N ratio in the detection of the signal voltage.

Using a bath voltage Vs and a bath resistance Rs between the reference electrode and the sensitive electrode, and an input impedance Rin of the potentiometer serving as a measuring circuit, a measured electric potential Vm of the potentiometer is expressed by the following equation.

$$Vm = Vs \cdot Rin/(Rs+Rin) \quad (1)$$

As apparent from this equation (1), to increase measurement accuracy—namely, to approximate the measured electric potential Vm to the bath voltage Vs, it is necessary to enlarge the input impedance Rin with respect to the bath resistance Rs so as to allow electric current to flow in the measuring circuit as less as possible. As the oil intervening these electrodes has a volume resistance of $10^8$ $\Omega$-cm, the bath resistance Rs becomes a fairly large value. Accordingly, the input impedance Rin needs to be enlarged in accordance with this bath resistance Rs. In fact, the Unexamined Japanese Patent Application No. HEI 3-175350/1991 discloses a potentiometer having an input impedance of approximately $10^{11}$.

However, realization of such a large resistance range is not easily attained by conventionally existing devices. Furthermore, a measuring circuit having such a large input impedance Rin will increase costs, because it requires a specially designed, sealed, structurally-integrated device to exclude moisture in the air and prevent leaks through the connectors.

Moreover, as it is believed that the pH value of the oil is representative of H ion density in water content involved in the oil, it was difficult to promote the electrochemical reactions around the sensitive electrode and, therefore, an output potential of the sensitive electrode could not be increased sufficiently. Hence, the S/N ratio obtained was insufficient.

SUMMARY OF THE INVENTION

Accordingly, in view of above-described problems encountered in the prior art, an object of the present invention is to provide an oil deterioration detector capable of preventing metallic oil devices, which perform as one of electrode, from giving adverse affection to the sensing electrodes (reference and sensitive electrodes), or obtaining sufficient S/N ratio by lowering the bath resistance between these sensing electrodes.

In order to accomplish above purposes, a first aspect of the present invention provides an oil deterioration detector comprising: a sensitive electrode whose electric potential varies in response to acidity and/or basicity of oil to be measured; a reference electrode associated with said sensitive electrode; an electrically conductive housing for accommodating said sensitive electrode and said reference electrode together with said oil; a potential difference detector for detecting oil deterioration by detecting a potential difference between said sensitive electrode and said reference electrode; and an insulating member interposed between said, electrodes and said electrically conductive housing for electrically insulating said electrodes from said electrically conductive housing.

A second aspect of the present invention provides an oil deterioration detector comprising: a sensitive electrode whose electric potential varies in response to acidity and/or basicity of oil to be measured; a reference electrode associated with said sensitive electrode; an electrically conductive housing for accommodating said sensitive electrode and said reference electrode together with said oil; a potential difference detector for detecting oil deterioration by detecting a potential difference between said sensitive electrode and said reference electrode; and either of said sensitive electrode and said reference electrode being set to have a predetermined referential electric potential identical with an electric potential of said electrically conductive housing.

Furthermore, a third aspect of the present invention provides an oil deterioration detector comprising: a sensitive electrode whose electric potential varies in response to acidity and/or basicity of oil to be measured; a reference electrode associated with said sensitive electrode; an electrically conductive housing for accommodating said sensitive electrode and said reference electrode together with said oil; a potential difference detector for detecting oil deterioration by detecting a potential difference between said sensitive electrode and said reference electrode; and an insulating, hydrophilic porous member being interposed between said sensitive electrode and said reference electrode.

BRIEF DESCRIPTION OF THE DRAWINGS

The above and other objects, features and advantages of the present invention will become more apparent from the following detailed description which is to be read in conjunction with the accompanying drawings, in which.

DETAILED DESCRIPTION OF THE PREFERRED EMBODIMENTS

Hereinafter, preferred embodiments of the present invention will be explained in detail with reference to the accompanying drawings.

First embodiment

Figure 1:
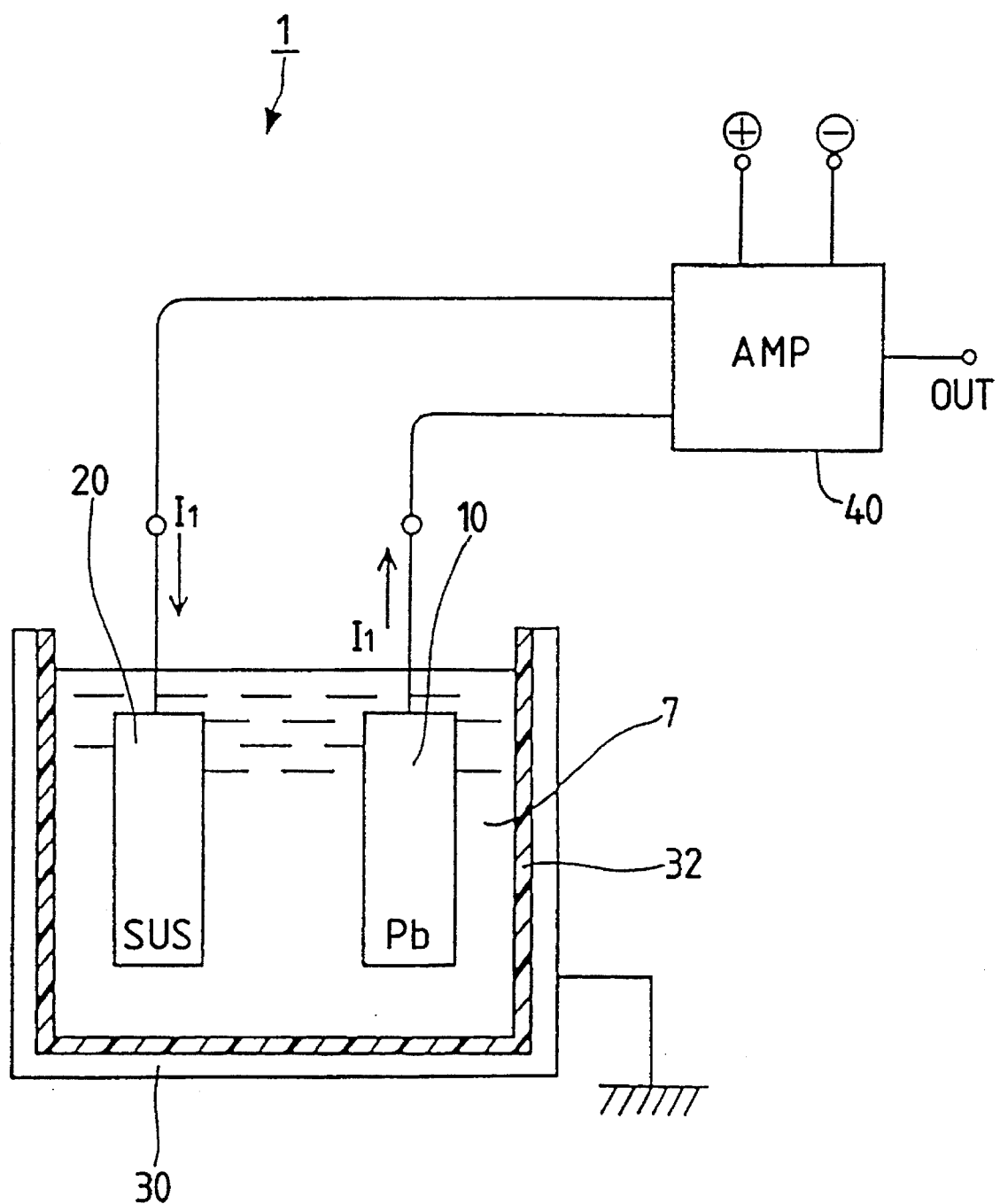
FIG. 1 is a schematic view showing an oil deterioration detector in accordance with the first embodiment of the present invention.

The first embodiment of the present invention will be explained with reference to FIG. 1.

An oil deterioration detector 1 comprises: a reference electrode 10 and a sensitive electrode 20, which are put or dipped into the measured oil 7 whose pH varies due to deterioration; an electrically conductive housing 30 accommodating the reference electrode 10 and the sensitive electrode 20 together with the measured oil 7; and a measuring device 40 detecting a potential difference between these electrodes 10 and 20.

The housing 30 is grounded. An insulating member 32 is provided between the housing 30 and the electrodes 10, 20 to prevent electric current from flowing between the housing 30 and the electrodes 10, 20.

This housing 30 is made of metal, such as aluminum alloy. The measured oil 7 is, for example, engine oil. The sensitive electrode 20 is a stainless steel electrode, while the reference electrode 10 is a lead electrode. The insulating member 32 is an insulating resin, such as PPS and Teflon, which is coated on the inside surface of the housing 30 and is durable against high temperature of the engine oil.

As the inside surface of the housing is coated by such an insulating member 32, no electric current can flow between the electrodes 10, 20 and the housing 30. This means that no leak current is caused. Therefore, the current flowing between the reference electrode 10 and the sensitive electrode 20 contains no measuring error. The insulating material 32 can have a sufficiently high insulating resistance even if its film thickness is very thin. Accordingly, the clearance between the electrodes 10, 20 and the housing 30 can be greatly shortened; thus, the size of the oil deterioration detector 1 can be fairly reduced compared with that of the conventional apparatus.

As described above, the oil deterioration detector in accordance with this first embodiment not only allows the reduction of size but brings higher accuracy in measurement by preventing any leak current from flowing between the electrodes and the housing.

Although this embodiment uses resin for the insulating member 32, it will be also preferable to form an alumite insulating layer on the inside surface of the aluminum alloy housing.

Second embodiment

Figure 2:
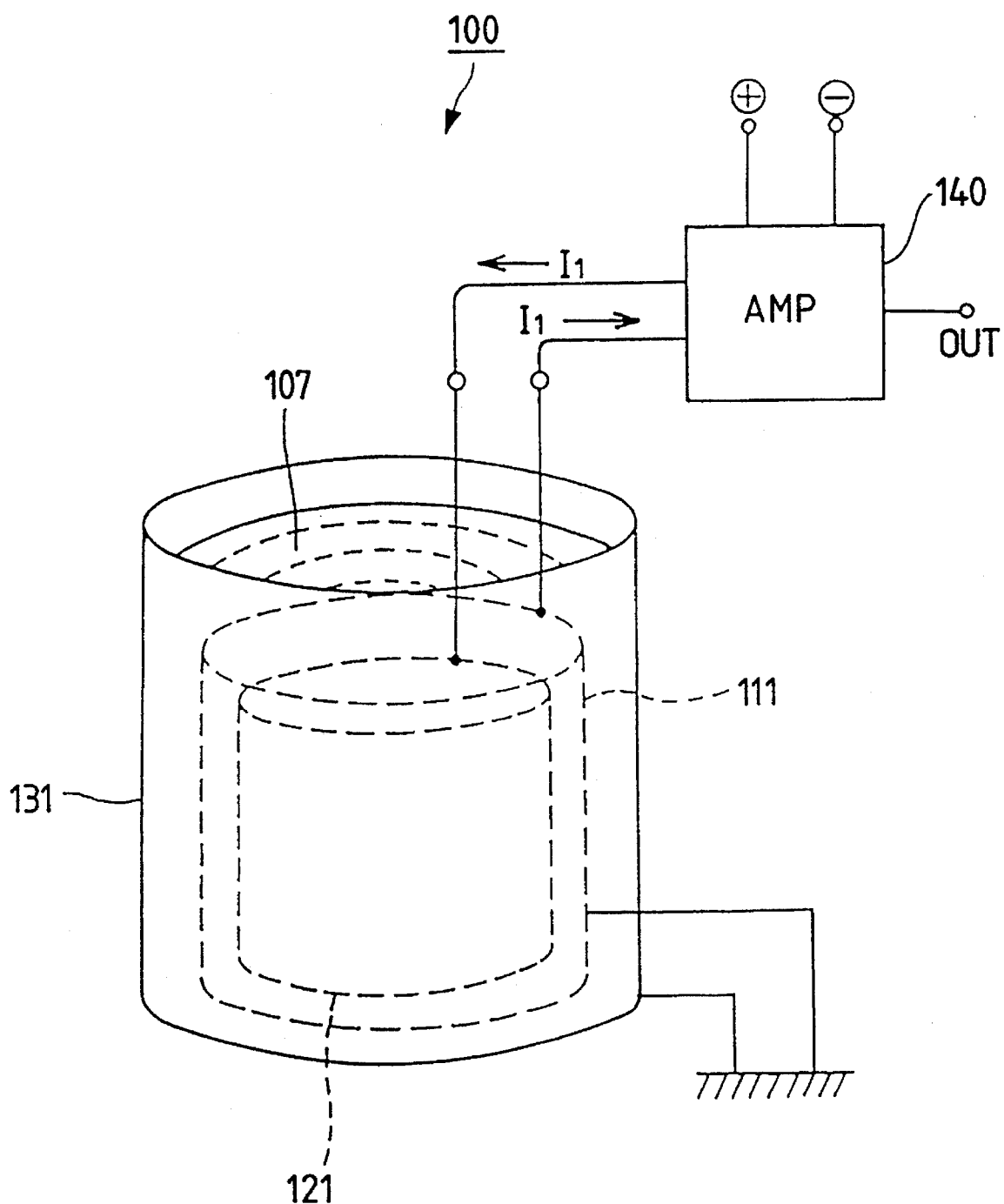
FIG. 2 is a schematic view showing an oil deterioration detector in accordance with the second embodiment of the present invention.

The second embodiment of the present invention will be explained with reference to FIG. 2.

An oil deterioration detector 100 comprises: a reference electrode 111 and a sensitive electrode 121, which are put or dipped into the measured oil 107 whose pH varies due to deterioration; an electrically conductive housing 131 accommodating the reference electrode 111 and the sensitive electrode 121 together with the measured oil 107; and a measuring device 140 detecting a potential difference between these electrodes 111 and 121.

The housing 131 is grounded. The housing 131 and the reference electrode 111 are electrically short-circuited. This housing 131 is a cylindrical tank made of metal, such as aluminum alloy, with a bottom. The reference electrode 111 and the sensitive electrode 121 have cylindrical shape and disposed coaxially with each other in the measured oil 107 filled in the housing 131.

Next, an operation of this second embodiment will be explained. It is preferable that the output impedance between the electrodes 111 and 121 of the oil deterioration detector 100 is small. The output impedance between the electrodes 111 and 121 of the oil deterioration detector 100 is reversely proportional to the areas of these electrodes 111 and 121 but proportional to the clearance between the electrodes 111 and 121. In short, it is preferable to enlarge the areas of the electrodes 111 and 121 and shorten the clearance between these electrodes 111 and 121.

As the reference electrode 111 and the sensitive electrode 121 of this embodiment are cylindrical and disposed coaxially, it is possible to widen the areas of the electrodes 111 and 121 and also to narrow the clearance between the electrodes 111 and 121 within a smaller volume compared with the flat electrodes.

Accordingly, without increasing the size of the oil deterioration detector, the output impedance between the electrodes 111 and 121 can be lowered.

Furthermore, in order to improve detection sensitivity, it is preferable to enlarge the passage area of the measured oil 107. In this respect, cylindrically shaped and coaxially disposed electrodes 111 and 121 of this embodiment are advantageous to enlarge the passage area of the measured oil 107 compared with the flat electrodes.

In the oil deterioration detector 100 in accordance with this embodiment, all the electric current flow from the inside sensitive electrode 121 to the outside reference electrode 111. Namely, even if the electric current flows directly into the housing 131, it does not result in the leak current since the housing 131 is short-circuited with the reference electrode 111. Accordingly, no measurement error is caused by the leak current.

Moreover, short-circuiting the reference electrode 111 and the housing 131 with a good conductor is very easy; thus, the size of the oil deterioration detector 100 needs not be increased.

Yet further, this embodiment does not require to maintain a large clearance between the reference electrode 111 and the housing 131 to reduce the impedance therebetween as was so in the conventional device. Therefore, the clearance between the reference electrode 11 and the housing 131 can be narrowed, thereby reducing the overall size.

As described above, the oil deterioration detector in accordance with the second embodiment not only allows the reduction of size but brings higher accuracy in measurement by preventing any leak current from flowing between the electrodes and the housing.

Third embodiment

Figure 3:
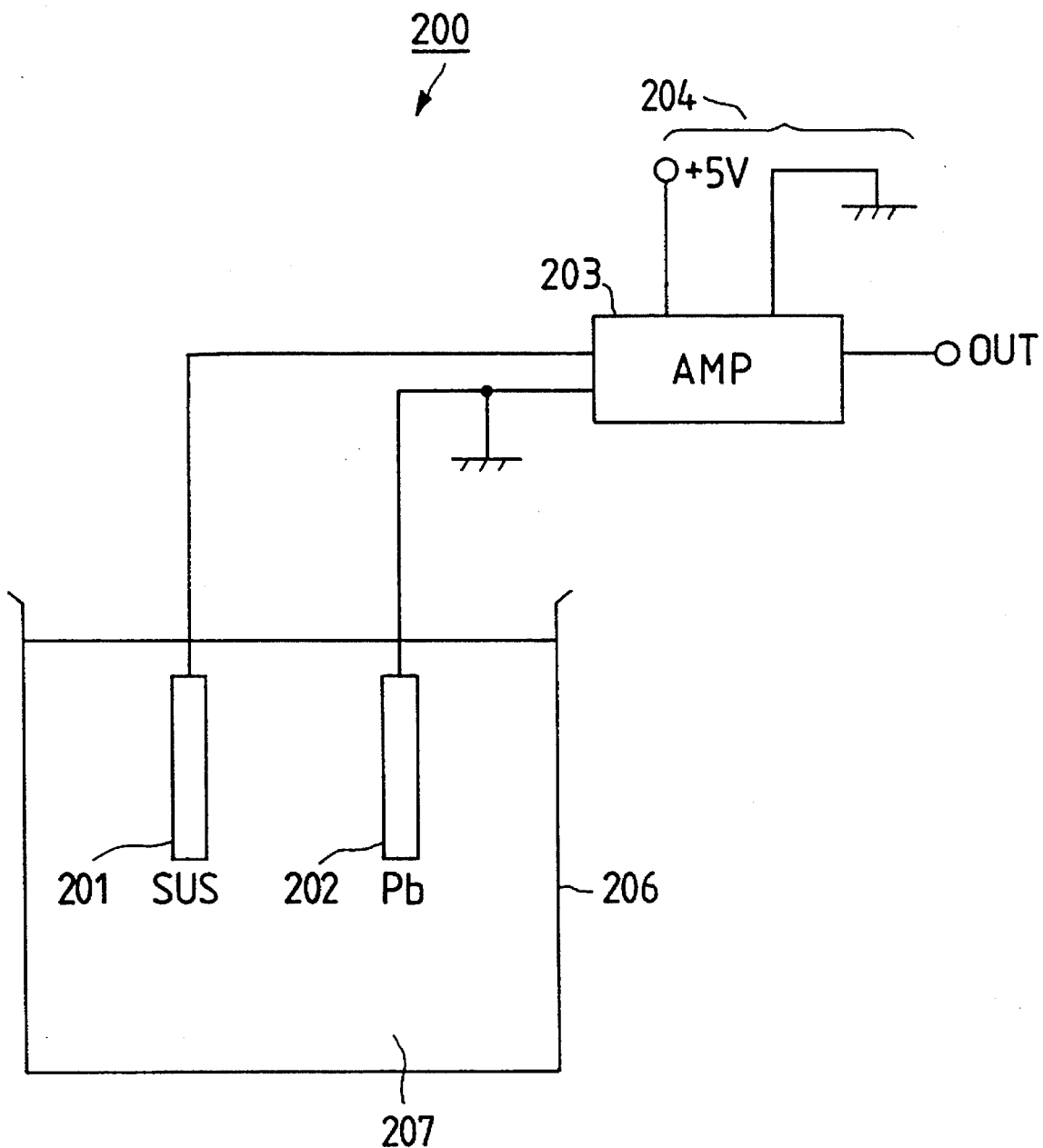
FIG. 3 is a schematic view showing an oil deterioration detector in accordance with the third embodiment of the present invention.

The third embodiment of the present invention will be explained with reference to FIG. 3.

An oil deterioration detector 200 comprises: a reference electrode 202 and a sensitive electrode 201, which are put or dipped into the measured oil 207 whose pH varies due to deterioration; an electrically conductive housing 206 accommodating the reference electrode 202 and the sensitive electrode 201 together with the measured oil 207; a differential amplifier 203 detecting a potential difference between these electrodes 201 and 202; and an electric power 204 for the differential amplifier 203.

In this third embodiment, the reference electrode 202 is grounded. Therefore, the electric potential of the sensitive electrode is always positive. The differential amplifier 203 amplifies the potential difference between these electrodes 201 and 202, and this differential amplifier 203 has an input range with a reference value identical with the electric potential of the reference electrode 202 (i.e. ground potential). And, the electric power 204 of the differential amplifier 203 can be a single electric power (i.e. single-end electric power).

Fourth embodiment

The fourth embodiment of the present invention will be explained with reference to FIGS. 4 to 8.

An engine block 301 is formed with an oil inlet opening 311 and an oil outlet opening 312. An oil cooler 302 and an oil filter 303 are successively mounted on the engine block 301 so as to be placed above these openings 311 and 312.

The oil cooler 302 includes a central cylinder 321 having a lower end threaded into the oil inlet opening 311 and extending upwardly. A housing 322 of the oil cooler 302 is coupled with this central cylinder 321. By using a presser screw 304 threaded around the central cylinder 321, the housing 322 is fixed together with a cover plate 322c on the engine block 301.

The housing 322 comprises: a central cylindrical portion 322a into which the central cylinder 321 is inserted; a bottom-opened cylindrical vessel portion 322b whose cylindrical wall is coaxially disposed with the central cylindrical portion 322a; and the cover plate 322c closing the lower opening of the bottom-opened cylindrical vessel portion 322b. A cooling water inlet 323 and a cooling water outlet 324 are formed on the cylindrical wall of the bottom-opened cylindrical vessel portion 322b.

Oil passing holes 325, passing oil to the oil filter 303, are opened on a top plate portion of the bottom-opened cylindrical vessel portion 322b. Oil passing holes 326, receiving oil from the oil outlet opening 312 of the engine block 301, are opened on the cover plate 322c.

Figure 4:
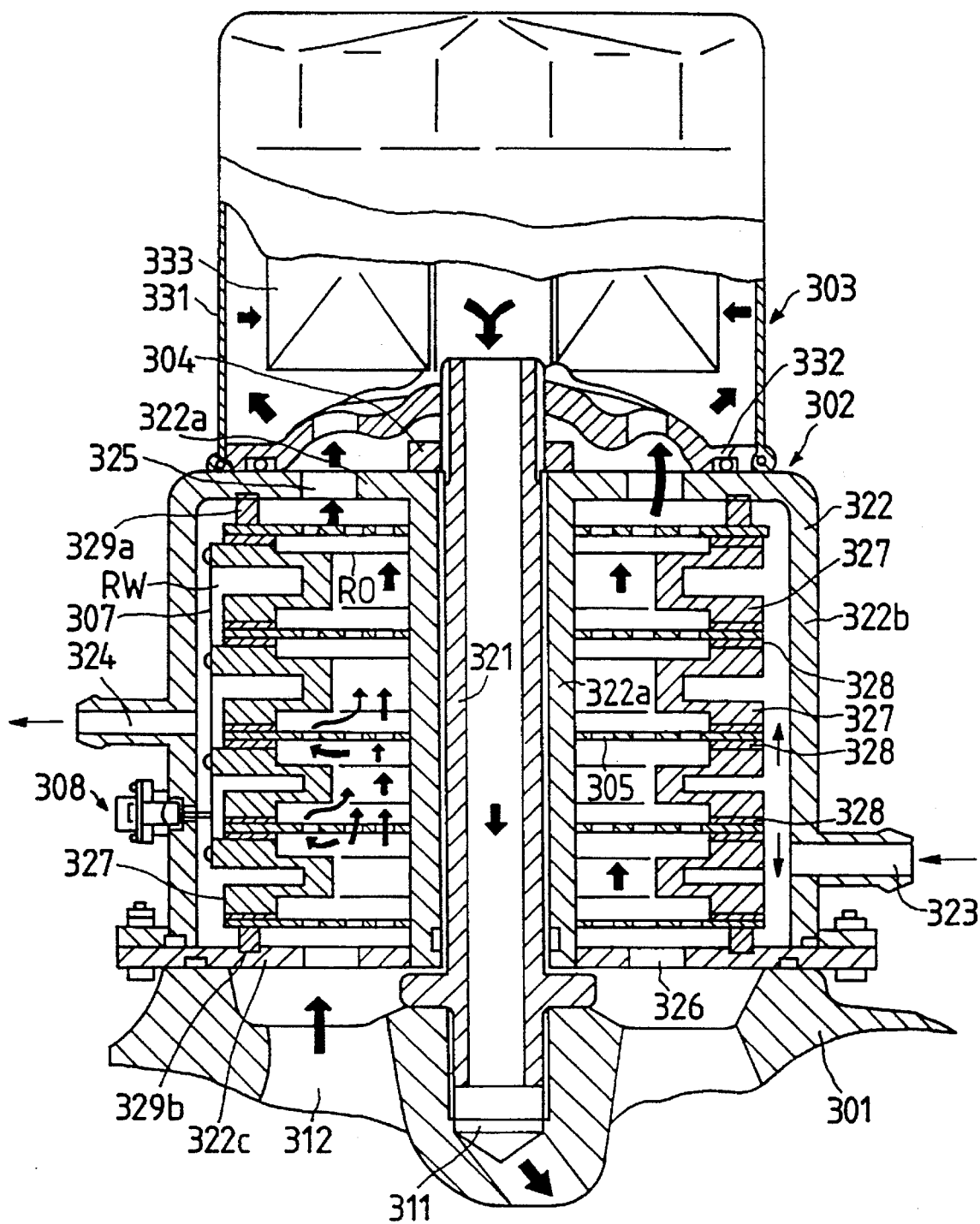
FIG. 4 is a partly broken view showing an oil purification device equipped with an oil deterioration detector in accordance with the fourth embodiment of the present invention.
Figure 5:
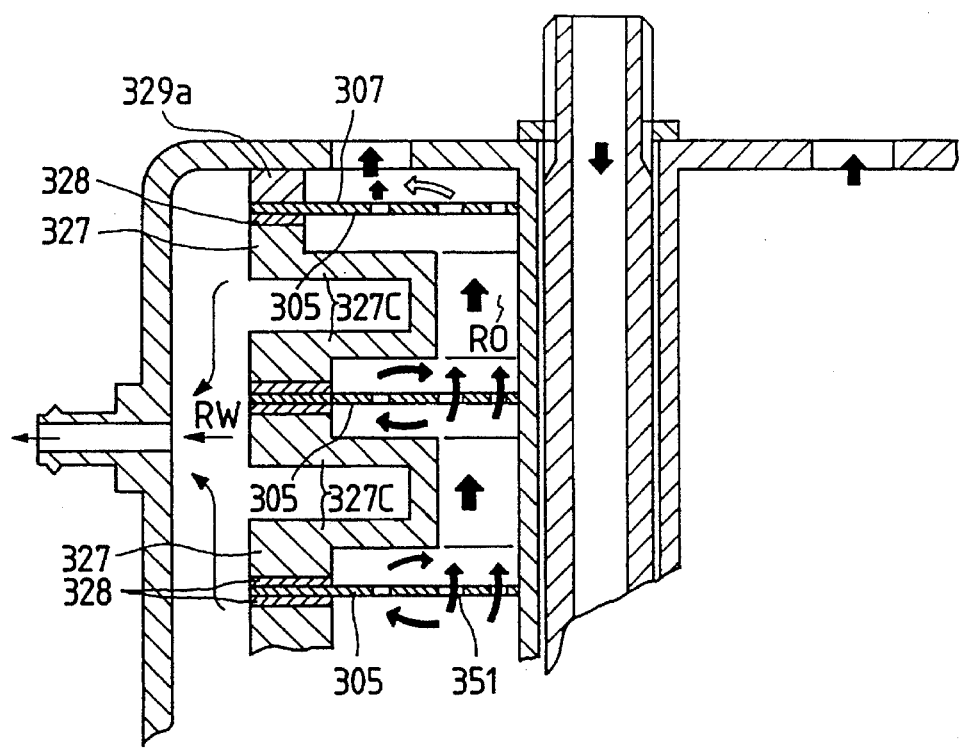
FIG. 5 is a partly enlarged view of FIG. 4.

The oil filter 303, whose axial and central portion is shown in the partly broken view of FIG. 4, comprises: a bottom-opened cylindrical vessel 331, a cover plate 332 covering the lower opening of the bottom-opened cylindrical vessel 331. This cover plate 332 has a screw hole at its central portion into which the central cylinder 321 is coupled, thereby fixing the oil filter 303 on the top plate portion of the bottom-opened cylindrical vessel portion 322b of the oil cooler 302. A filter unit 333 is accommodated in the bottom-opened cylindrical vessel 331.

Next, the inside structure of the oil cooler 302, which constitutes an essential part of this embodiment, will be explained in more detail. In the oil cooler 302, there is provided a total of four cylindrical radiators 327, - - -, 327 piled up in the axial direction coaxially with the central cylinder 321. Each of these cylindrical radiators 327, - - -, 327 is formed with a pair of larger-diameter portions provided at its axially upper and lower ends and a smaller-diameter portion provided at its axially central portion; thus, an overall heat transfer (radiating) area is sufficiently large. Namely, disk-like portions 327c, 327c are provided on the cylindrical radiator 327 between the axially upper and lower ends and the axially central portion.

A metallic disk 305 is interposed between adjacent two cylindrical radiators 327 and 327. Also, metallic disks 305, 305 are disposed on the upper surface of the uppermost cylindrical radiator 327 and the lower surface of the lowermost cylindrical radiator 327. Namely, a total of five metallic disks 305, 305, 305 is provided for four cylindrical radiators 327, - - - 327. The ring-shaped upper and lower end surfaces of each cylindrical radiator 327 are connected with the metallic disk 305 through ring-shaped resin spacers 328, 328, thereby defining an oil chamber Ro inside the cylindrical radiator 327.

Furthermore, the upper surface of the uppermost metallic disk 305 and the lower surface of the lowermost metallic disk 305 are connected with ring-shaped resin spacers 329a and 329b. These ring-shaped resin spacers 329a and 329b are connected with the top plate portion of the bottom-opened cylindrical vessel portion 322b and the cover plate 322c, respectively, thereby comparting the oil chambers Ro from a cooling water chamber Rw surrounding the oil chambers Ro.

The cylindrical radiators 327, - - -, 327 and the metallic disks 305, - - -, 305 are made of stainless steel. An oxide film layer of approximately 2 to 10 μm is formed on the surface of the cylindrical radiator 327, while a lead layer of approximately 20 to 30 μm is plated on the surface of the metallic disk 305. A radially central portion of the metallic disk 305 confronts with and is axially spaced from the disk-like portion 327c of the cylindrical radiator 327 with a gap of approximately 1.5 mm. A radially inward end of the metallic disk 305 is brazed or welded onto the central cylindrical portion 322a of the housing 322; therefore, the metallic disk 305 is electrically grounded through the central cylindrical portion 322a. Furthermore, a plurality of oil passing holes 351, - - - 351 (refer to FIG. 5) are opened on the metallic disk 305. Oil flows from the oil outlet opening 312 of the engine block 301 to the oil chamber Ro in the oil cooler 302, the oil filter 303 and the central cylinder 321, and returns to the oil inlet opening 311 of the engine block 301.

A copper cable 307, sheathed by insulating material, is soldered on the outer peripheral end of each cylindrical radiator 327. One end of this copper cable 307 is connected to an amplifier 308 installed on the outer peripheral surface of the bottom-opened cylindrical vessel portion 322b of the oil cooler 302 to transmit a detected signal. Of course, the copper cable 307 is electrically insulated from the housing 322 of the oil cooler 302.

Figure 6:
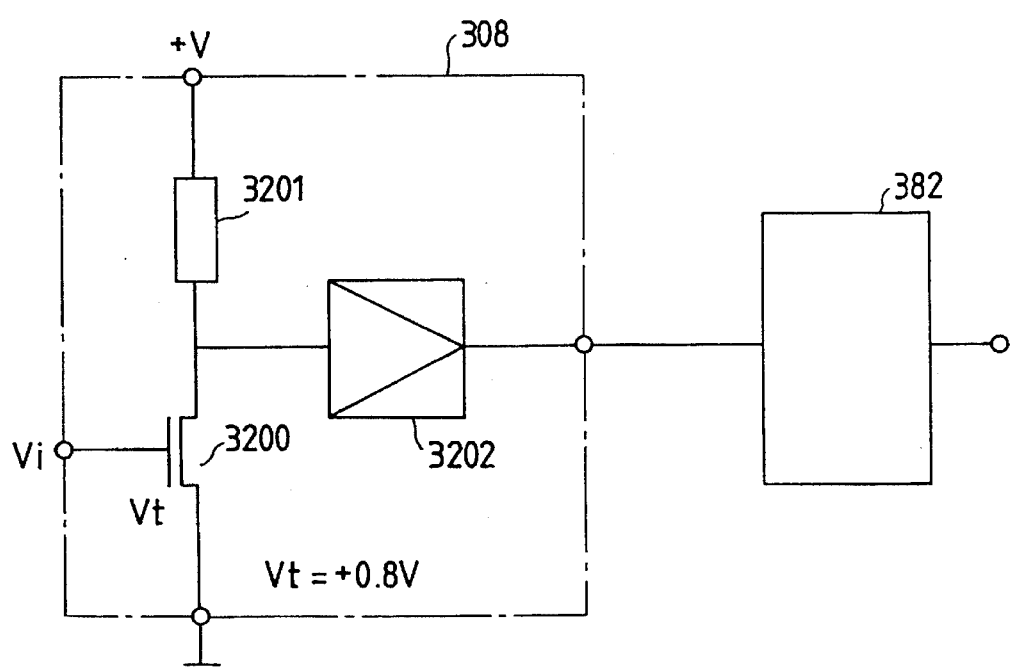
FIG. 6 is a circuit diagram showing a preferable amplifier in accordance with the fourth embodiment.

The cylindrical radiator 327 in the oil cooler 302 removes heat from the oil and discharges it to the cooling water. The oil filter 303 purifies the oil. After passing through the oil filter 303, the oil returns the engine block 301. According to this embodiment, the cylindrical radiator 327, electrically insulated from the housing 322 of the oil cooler 302, confronts with the metallic disk (metallic electrode) 305 with a tiny gap. Therefore, an electric potential is caused between the cylindrical radiator 327 and the metallic disk 305. As the metallic electrode 305 is grounded, the cylindrical radiator 327 generates a positive signal voltage less than 1 V. This signal voltage is amplified in the amplifier 308 as shown in FIG. 6, and is, thereafter, input into the A/D converter equipped engine control unit 382.

In this embodiment, both the oil cooler 302 and the housing 322 are made of stainless steel. Hence, the oil in the oil chamber Ro partly contacts with the stainless steel of the housing 322. However, as the confronting area between the cylindrical radiator 327 and the metallic disk 305 is very large in this embodiment, the electric potential between the cylindrical radiator 327 and the metallic disk 305 mainly determines the electric potential of the cylindrical radiator 327.

Characteristic features of this embodiment will be explained hereinafter.

As the cylindrical radiator 327 of the oil cooler 302 of the present invention serves as an electrode sheathed by the insulating material, the oil cooler 302 needs not to increase its volume and weight. Also, no additional space is required for installing the oil deterioration detector. Furthermore, the metallic disk 305 is effective to cool down the oil.

Figure 7:
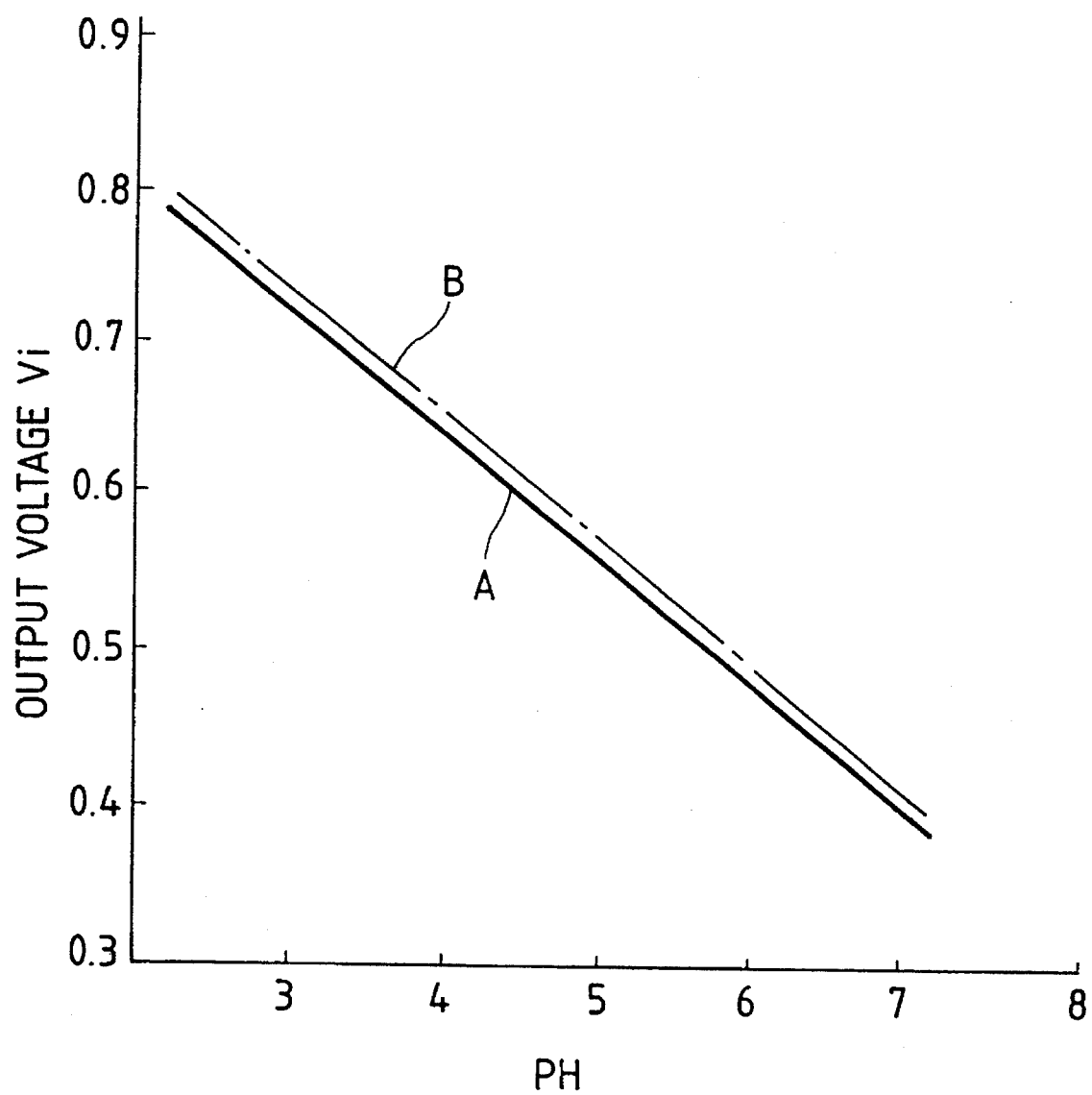
FIG. 7 is a graph showing the output characteristics of the oil deterioration detector in accordance with the fourth embodiment.

In FIG. 7, an alternate long and short dash line B indicates the output characteristics of this oil deterioration detector in which the metallic electrode (reference electrode) is grounded. In this case, the pH of the oil is measured in advance. A solid line A indicates the output characteristics of an oil deterioration detector in which the metallic disk 305 is electrically insulated from the housing 322. It is understood that the output voltage of B is always higher than the output voltage of A. It is also understood that the electric potential of the cylindrical radiator 327 increases with reducing pH of deteriorated oil. It is believed that the cylindrical radiator 327 absorbs the hydrogen ions isolated from the oil.

Above-described electric potential increase is advantageous in amplifying the signal voltage in the amplifier 308. Namely, in a vehicle oil deterioration detector, the amplifier 308 is generally supplied with electric power from a vehicle battery (not shown). The electric power of vehicle batteries is normally positive (i.e. +12 V). Accordingly, the constitution of the amplifier 308 would be most simple when the amplifier 308 operates by a positive, single, electric power voltage source. In this respect, this embodiment enables to input a positive signal voltage Vi into the amplifier 308 by grounding the metallic disk 305 and electrically insulating the cylindrical radiator 327 from the housing 322.

FIG. 6 shows a circuit of a preferable example of the amplifier 308. This circuit includes an enhancement type nMOS transistor 3200 and its load resistance 3201. This transistor 3200, serving as a first-stage voltage amplifier, has a large input resistance and has a source grounded. A threshold value of the transistor 3200 is 0.8 V. When the output voltage Vi increases at 0.8 V due to deterioration of oil, a low-level voltage is input into the second-stage power amplifier 3202 and, then, the power amplifier 3202 outputs a signal voltage corresponding to the input voltage.

More specifically, the transistor 3200 in this circuit is in an OFF condition when the oil is clean. Therefore, an ON voltage (threshold voltage) of this transistor 3200 can be used as a threshold value for making a judgement of oil deterioration. It means that the circuit construction is very simplified.

Furthermore, no complicated operational amplifier requiring two electric power sources for operation is needed. Of course, the circuit can be constituted in a feedback circuit. Accordingly, nevertheless the metallic disk (metallic electrode) 305 is grounded, it becomes possible to amplify a signal voltage by the amplifier 308 which has a large input impedance and is operable by a single electric power source. Similar effect will be obtained even if the first-stage voltage amplifier of the amplifier 308 is replaced by a CMOS invertor.

Figure 8:
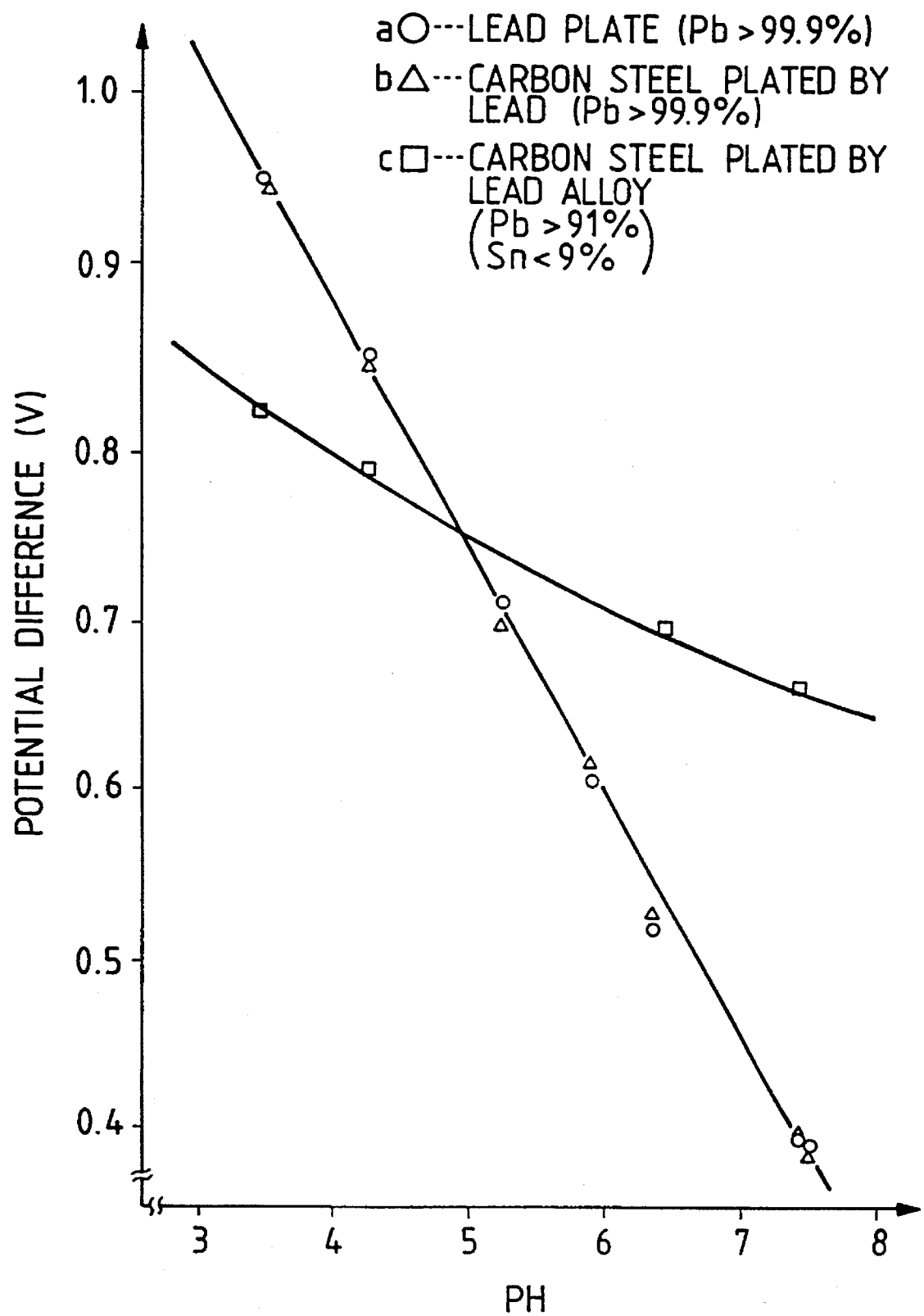
FIG. 8 is a graph showing test result measuring the potential difference with respect to various pH of oil in accordance with the fourth embodiment.

FIG. 8 shows test result measuring a potential difference with respect to various pH of oil. In this test, a stainless steel plate is sheathed by an oxide film layer with the same thickness as the above-described one, to provide an electrode of the present invention, which is sheathed by insulating material. Meanwhile, for the other electrode, a lead plate (a in FIG. 8), a carbon steel plated by lead (b in FIG. 8) and a carbon steel plated by lead alloy (Pt 91 wt %, Sn 9 wt %, c in FIG. 8) are used.

Fifth embodiment

Figure 9:
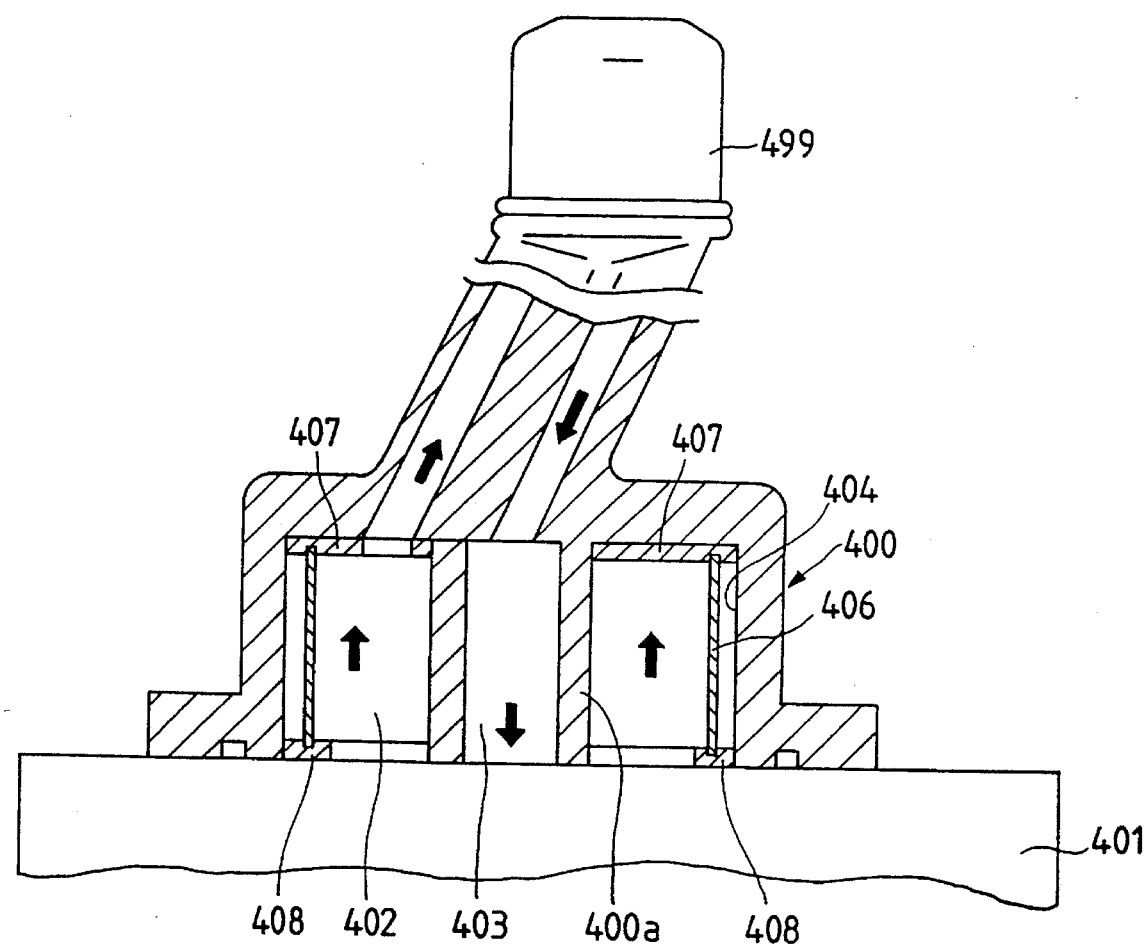
FIG. 9 is an oil purification device in accordance with the fifth embodiment of the present invention.

The fifth embodiment of the present invention will be explained with reference to FIG. 9. In this embodiment, an oil filer 499 is mounted on a mount member 400 which is fixed on an engine block 401. The mount member 400 includes an oil going passage 402 and an oil returning passage 403 which are coaxially provided.

The oil enters from the engine block 401 to the oil filter 499 through the oil going passage 402. After the oil is purified in the oil filter 499, the oil returns the engine block 401 through the oil returning passage 403.

In this embodiment, a lead layer (not shown) is formed on an inner peripheral surface 404 of the oil going passage 402. A cylinder 406, with upper and lower open ends and made of stainless steel plate sheathed by oxide material, is placed in the oil going passage 402 so as to confront with the lead layer of the inner peripheral surface 404 with a gap of approximately 1.5 mm. This cylinder 406 is supported by resin plates 407 and 408 at the upper and lower ends thereof, so that the cylinder 406 is electrically insulated from the mount member 400 and the engine block 401. The cylinder 406 has numerous holes opened thereon, so as to allow the oil to pass through these holes.

It is preferable that an outer peripheral surface of a central cylinder portion 400a of the mount member 400 is also plated by lead.

Although the entire surface of the metallic disk is plated by lead, it will be acceptable to apply plating partly. This embodiment will allow to use zinc, tin, indium, cadmium, magnesium, or their alloys for plating material, instead of lead. Furthermore, metals or their alloys having an oxide film layer thereon, such as nickel, titanium, niobium, tantalum, zirconium, aluminum can be used as the electrode sheathed by insulating material. Or it will be possible to utilize the carbon steel constituting the main portion of the oil devices as the metallic disk—i.e. the metallic electrode of the present invention. In any case, the cylindrical radiator will cause a positive potential with respect to the metallic disk.

Sixth embodiment

Figure 12:
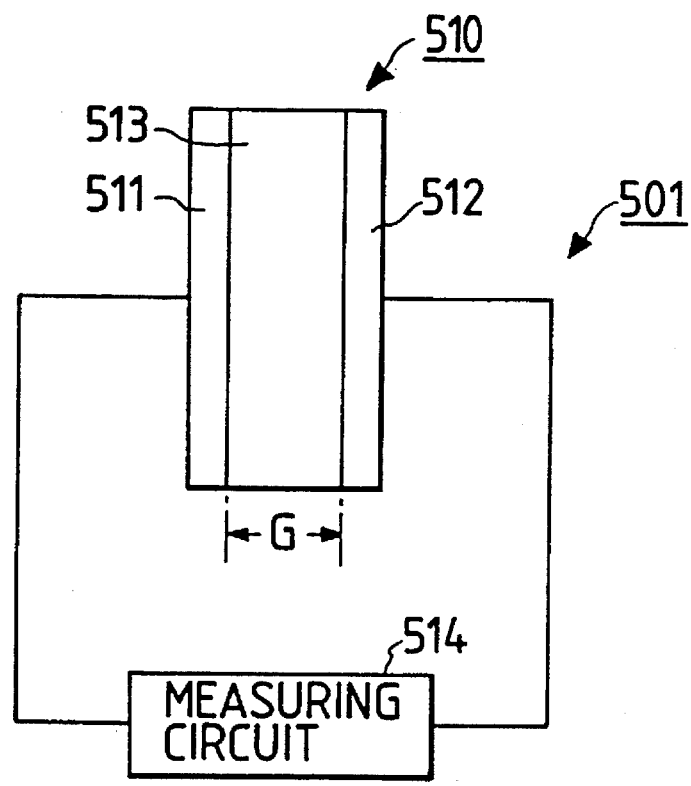
FIG. 12 is a schematic view showing an oil deterioration detector in accordance with the sixth embodiment of the present invention.

The sixth embodiment of the present invention will be explained with reference to FIGS. 12 and 13. FIG. 12 shows a basic principle of an oil deterioration detector in accordance with the sixth embodiment. The oil deterioration detector 501 comprises the paired electrodes 510 and the measuring circuit 514. The paired electrodes 510 includes a reference electrode 511 and a sensitive electrode 512. A fixed layer 513 is provided between the reference electrode 511 and the sensitive electrode 512, so as to provide a distance G between these electrodes 511 and 512.

The reference electrode 511 is a lead electrode formed into a predetermined shape. The surface of this electrode 511 is cleaned by dilute nitric acid and, then, washed by water and dried.

The sensitive electrode 512 is a stainless steel plate (SUS304) formed into the same shape as the reference electrode 511. An oxide film layer is formed on the surface of this stainless steel plate. This oxide film layer is formed by exposing a cleaned stainless steel in the atmosphere for 30 to 60 minutes at the temperature of 400° to 500° C.

The fixed layer 513, interposed between the electrodes 511 and 512, is constituted by laminating a hydrophilic filter having the porous structure of 35 μm thickness (for example, product name: hydrophilic PTFE type membrane filter H100A, by TOYO FILTERS Co. Ltd), and thereafter, fixing these laminated layers between the electrodes 511 and 512 by means of insulating bolts. This hydrophilic filter has a hole diameter of 1.0 μm and the porous degree of 83%. As this fixed layer 513 has insulating porous structure, this fixed layer 513 does not obstruct the electrochemical reactions occurring between these electrodes 511 and 512.

The measuring circuit 514 is connected to the electrodes 511 and 512 to measure an electric potential Vm (refer to FIG. 13) between the electrodes 511 and 512.

Figure 13:
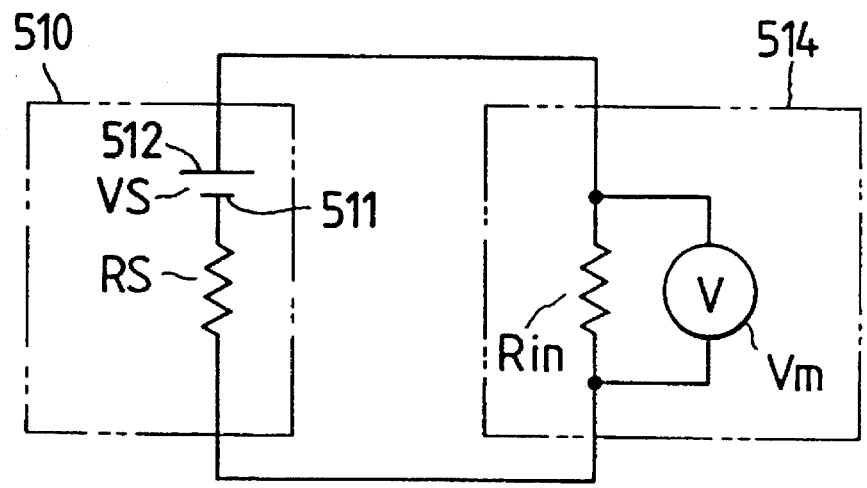
FIG. 13 is an equivalent circuit of the sixth embodiment of the present invention.

FIG. 13 shows an equivalent circuit of this embodiment. Using a bath voltage Vs and a bath resistance Rs between the reference electrode 511 and the sensitive electrode 512, and an input impedance Rin of the measuring circuit 514, the measured electric potential Vm is expressed by the above-described equation 1 (Namely, $Vm=Vs \cdot Rin/(Rs+Rin)$).

As apparent from this equation 1, to increase measurement accuracy—namely, to approximate the measured electric potential Vm to the bath voltage Vs, it is necessary to enlarge the input impedance Rin with respect to the bath resistance Rs so as to allow electric current to flow in the measuring circuit 514 as less as possible.

In accordance with this embodiment, the moisture contained in the oil concentrates in the region between electrodes 511 and 512 since the fixed layer 513 has hydrophilicity. Therefore, the bath resistance Rs reduces and the output voltage increases, resulting in improvement of measurement accuracy. Accordingly, the input impedance Rin of the measuring circuit 514 of the oil deterioration detector 501 will fall within the range of existing devices. Furthermore, as the output voltage of the sensitive electrode 512 increases, the S/N ratio of the oil deterioration detector 501 is improved.

Seventh embodiment

Figure 14:
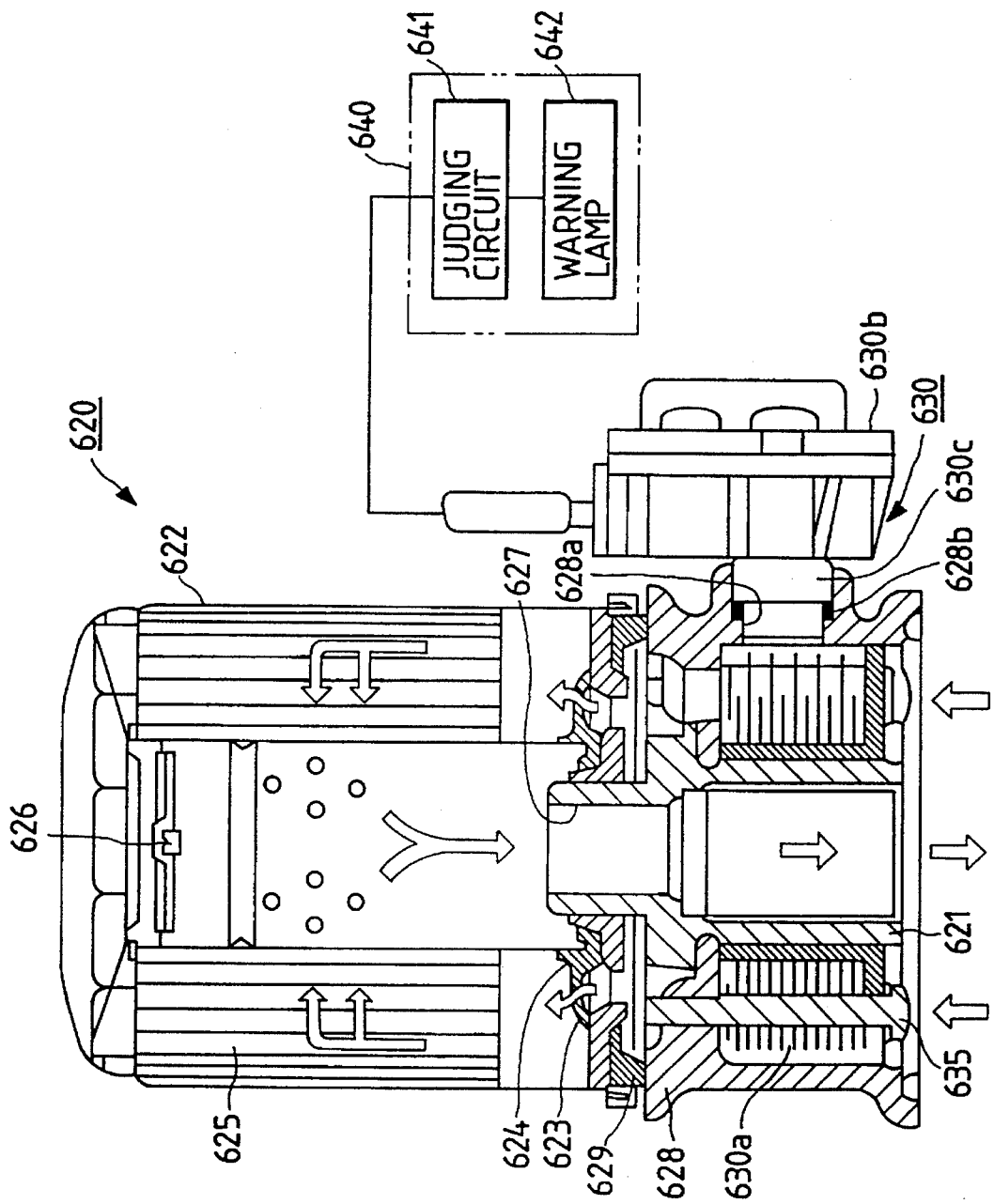
FIG. 14 is an oil purification device equipped with an oil deterioration detector in accordance with the seventh embodiment of the present invention.
Figure 15:
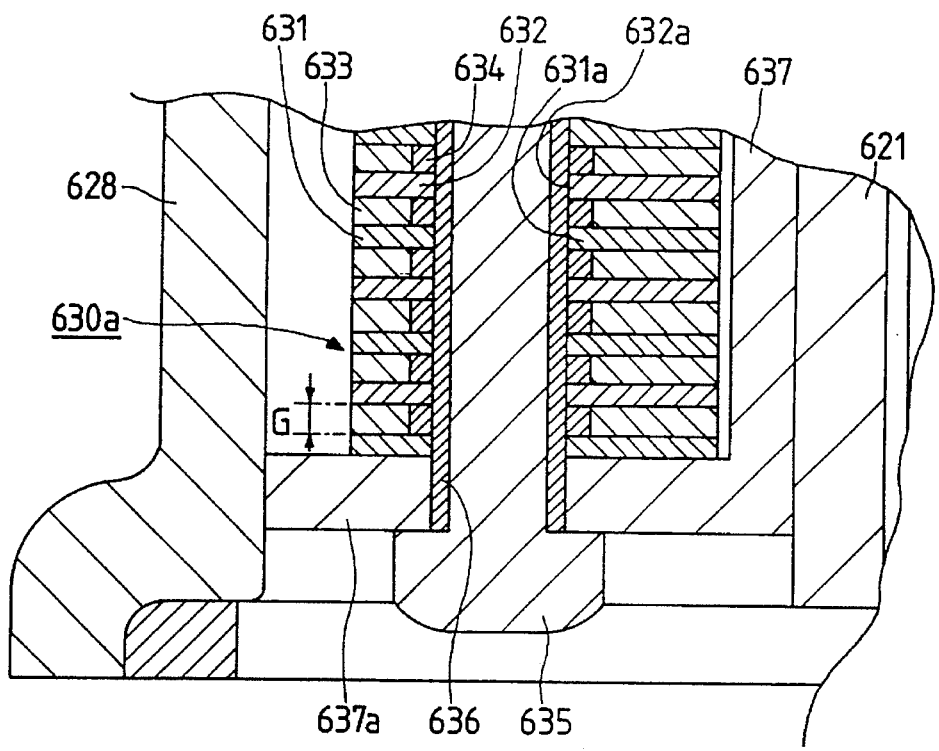
FIG. 15 is a partly enlarged view of FIG. 14.
Figure 16:
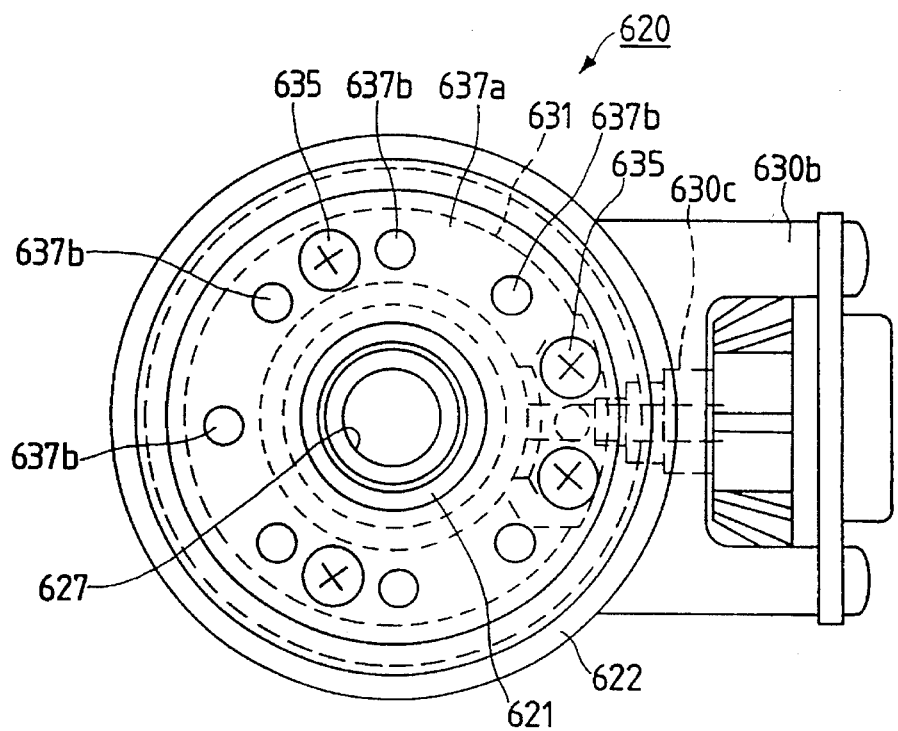
FIG. 16 is a bottom view of FIG. 14.

The seventh embodiment of the present invention will be explained with reference to FIGS. 14 to 18. FIG. 14 is a schematic diagram showing an oil purification device equipped with an oil deterioration detector. FIG. 15 is a partly enlarged view of FIG. 14. FIG. 16 is a bottom view of FIG. 14.

An oil purification device 620, equipped with an oil deterioration detector, comprises a union 621 connected to an engine block, an oil filter 622 connected by thread engagement to the upper part of the union 621, and a housing 628 connected by thread engagement to the lower part of the union 621. The oil filter 622 and the housing 628 are connected through a gasket 629.

The oil filter 622, a general full-flow type as shown in FIG. 14, comprises: oil inlets 623, 623 communicating with the inside of the housing 628; check valves 624, 624 associated with these oil inlets 623, 623; an element 625 purifying the oil introduced through the check valves 624, 624; a relief valve 626 opened in the event of blinding or cold start of the engine; and an oil outlet 627 supplying the oil to the lubrication portions of the engine.

An oil deterioration detector 630 comprises an electrode portion 630a and a sensor amplifier 630b. The electrode portion 630a is disposed in the housing 628 so as to be put or dipped into the oil. As illustrated in FIG. 15, the electrode portion 630a includes a plurality of reference electrodes 631 and sensitive electrodes 632. There are provided a plurality of spacers 634 so that each of these spacers 634 is interposed between one of the reference electrodes 631 and one of the sensitive electrodes 632. And, a plurality of fixed layers 633 are respectively disposed in the clearance G (G=1 mm) provided by each spacer 634. Thus, the reference electrodes 631 and the sensitive electrodes 632 are alternately piled up with clearances G. A bolt 635 is used to fix the electrode portion 630a. That is, the bolt 635 is inserted into the bolt insertion holes 631a and 632a opened on the electrodes 631 and 632. A cylindrical, insulating ring 636 is coupled around the bolt 636. Hence, the electrodes 631 and 632 are not short-circuited by the bolt 635.

The reference electrode 631 is a doughnut-shaped, lead electrode, with a plurality of oil passing holes (not shown) and a bolt insertion hole 631a. The surface of this reference electrode 631 is cleaned by dilute nitric acid and, then, washed by water and dried. These reference electrodes 631 have a total of 100 $cm^2$ confronting area.

The sensitive electrode 632 is a doughnut-shaped, stainless steel electrode (SUS304), with a plurality of oil passing holes (not shown) and a bolt insertion hole 632a. The surface of this stainless steel electrode is formed with an oxide film layer. This oxide film layer is formed by the same method as in the sixth embodiment.

The fixed layer 633, interposed between the electrodes 631 and 632, is constituted by laminating a hydrophilic filter having the porous structure of 35 μm thickness (e.g. product name: hydrophilic PTFE type membrane filter H100A, by TOYO FILTERS Co. Ltd), and thereafter, and interposing this united laminated layers between the electrodes 631 and 632 through the cylindrical spacer 634. The bolt 635 fixes this electrode portion 630a to the housing 628 through a flange portion 637a of a cylindrical sleeve 637. This hydrophilic filter has a hole diameter of 1.0 μm and the porous degree of 83%. As this fixed layer 633 has insulating porous structure, this fixed layer 633 does not obstruct the electrochemical reactions occurring between these electrodes 631 and 632.

Figure 17:
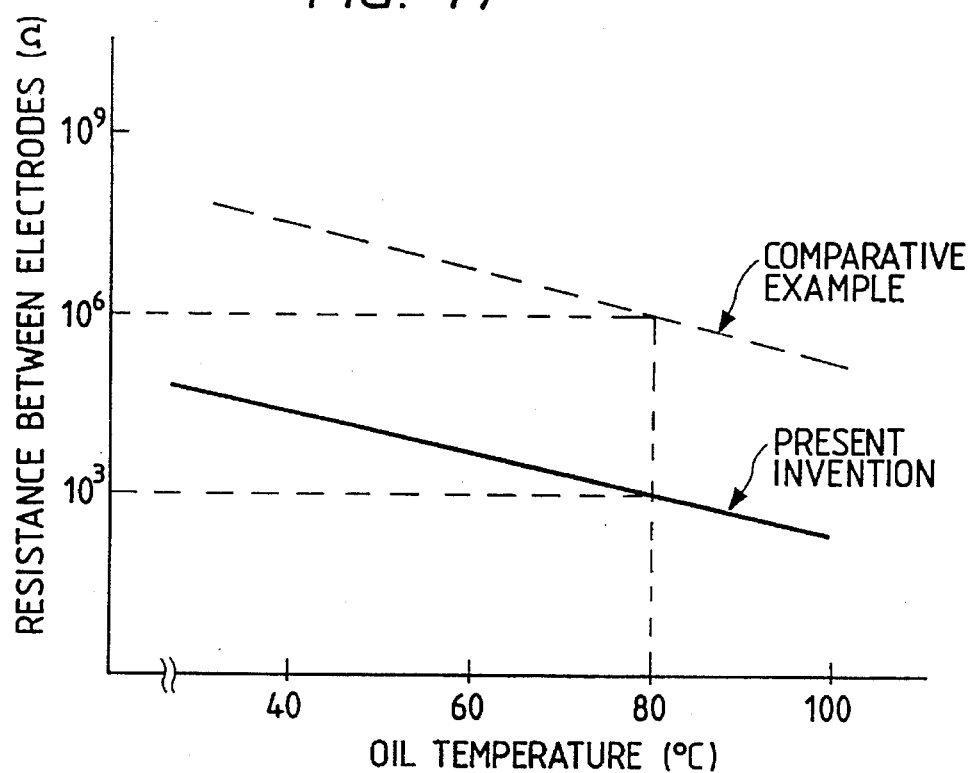
FIG. 17 is the test result showing the resistance between electrodes with respect to various oil temperatures.

By putting or dipping this electrode portion 630a into green test oil, the bath resistance between the reference and sensitive electrodes is measured with respect to oil temperatures. A solid line of FIG. 17 shows the result of this test. A dotted line of FIG. 17 shows the result of the comparative example in which the space between the electrodes 631 and 632 is filled with oil not the fixed layer 633. As apparent from FIG. 17, the bath resistance for the oil temperature 80° C. is $10^6$ Ω in the comparative example and $10^3$ Ω in the present invention device. The reason why the bath resistance is so greatly reduced in this invention is that the moisture contained in the oil concentrates in the region between the electrodes 631 and 632 since the fixed layer 633 has hydrophilicity. In general, moisture has a volume resistance smaller than that of oil. Therefore, the bath resistance Rs reduces and the output voltage increases, resulting in improvement of measurement accuracy.

Figure 18:
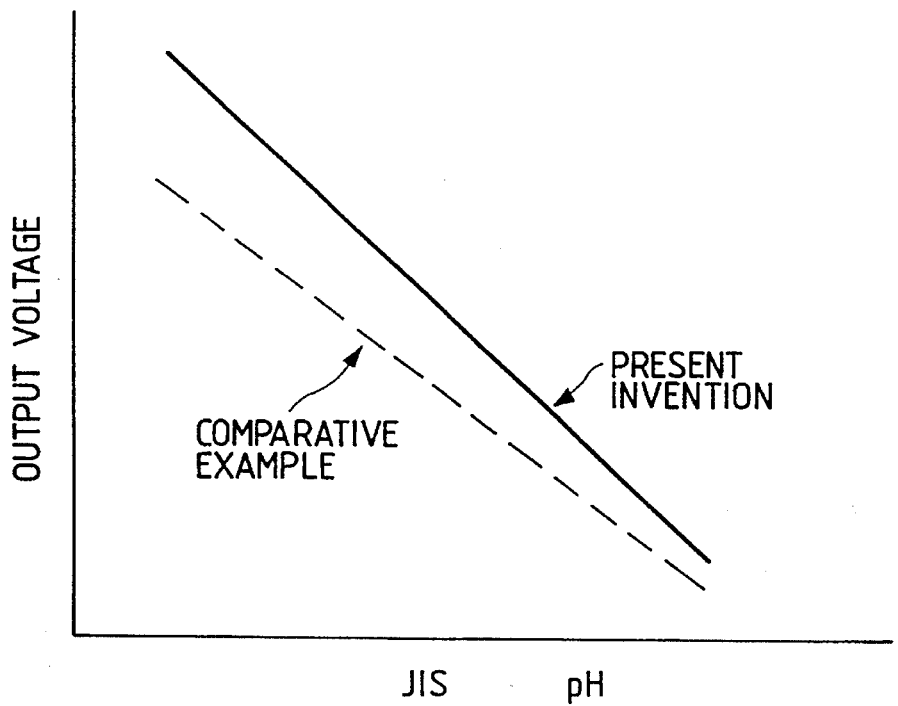
FIG. 18 is the test result showing the output voltage with respect to various pH of oil.

Using the electrode portion 630a, the output voltage is measured with respect to various pH of oil. A sold line of FIG. 18 shows the result of this test. A dotted line indicates the result of the comparative example which does not interpose the fixed layer 633 between the electrodes 631 and 632. As apparent from FIG. 18, the present invention device generates output voltages higher than those of the comparative example. A gradient of the output voltage is higher in the present invention device than in the comparative example. For these reasons, the S/N ratio is improved. It is believed that H ion density is higher in the region between the electrodes 631 and 632 since the moisture contained in the oil concentrates in this region, and therefore, the equilibrium between the deoxidation reaction of the metallic oxide and the oxidation reaction of metallic hydroxide occurring on the oxide film layer of the sensitive electrode 632 shifts toward the deoxidation reaction.

The sensor amplifier 630b is, as illustrated in FIG. 14, connected to the electrode portion 630a. A connecting portion 630c of the sensor amplifier 630b is coupled into an insertion hole 628a formed on the housing 628 through an O ring 628b, thereby placing the sensor amplifier 630b outside the housing 628. The sensor amplifier 630b is connected to a display unit 640. As the bath resistance is remarkably small compared with the comparative example the input impedance Rin of this sensor amplifier 630b falls within the range of existing devices.

The display unit 640 comprises a judging circuit 641 and a warning lamp 642. The judging circuit 641, including well-known comparators and others, compares an output voltage from the sensor amplifier 630b with a predetermined threshold value, and generates an output signal to turn of the warning lamp 642 when the output voltage from the sensor amplifier 630b exceeds the predetermined threshold value. The warning lamp 642 is located on an instrument panel of an automotive vehicle, to notify the driver of necessity of oil exchange in accordance with the output signal from the judging circuit 641. It is needless to say that the judging circuit 641 can be constituted by a micro computer. The above-described predetermined threshold value is a value corresponding to the pH (e.g. 3.5) of deteriorated oil.

Warning Lamp Control

Figure 10A:
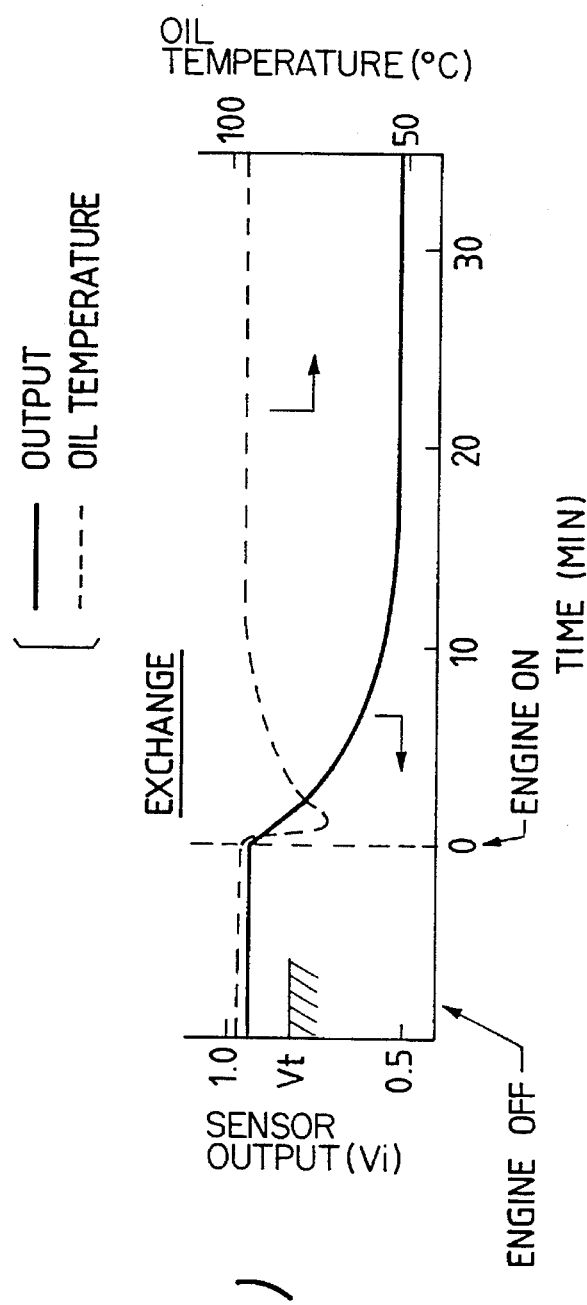
FIGS. 10(A) and 10(B) are time charts showing the changes of a sensor output and an oil temperature.
Figure 10B:
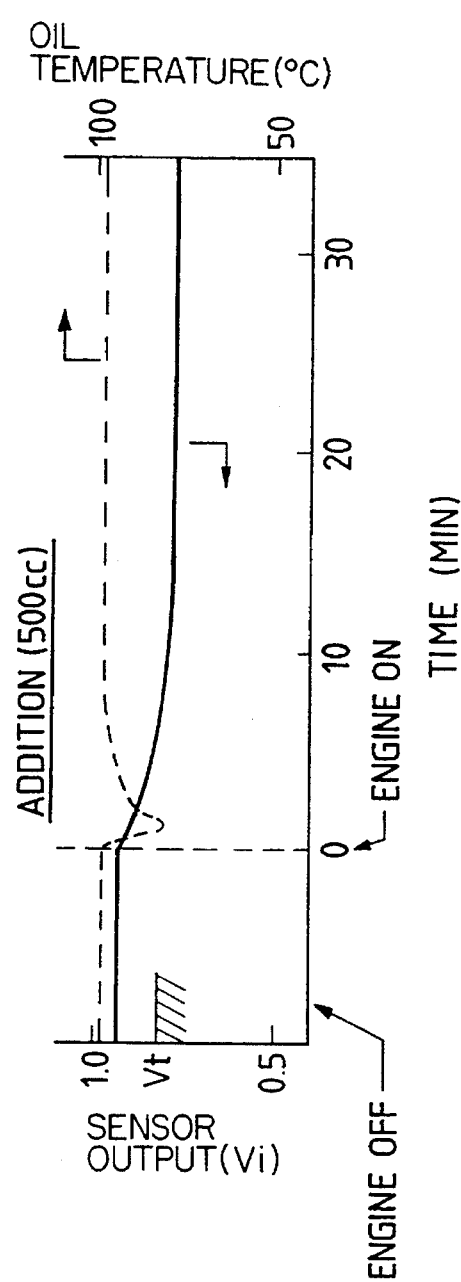
Figure 11:
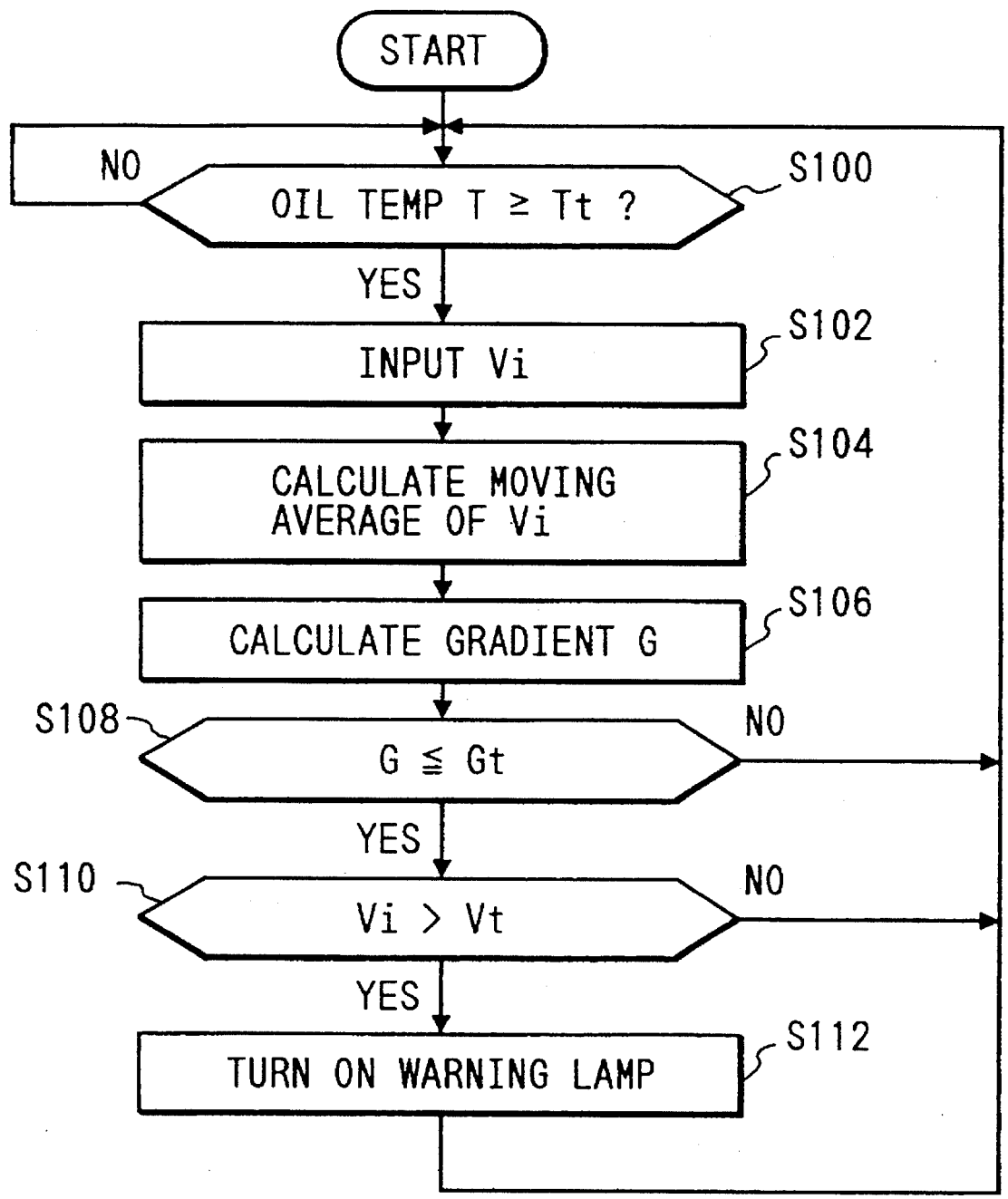
FIG. 11 is a flowchart showing a preferable control of a warning lamp in accordance with the present invention.

FIGS. 10(A), 10(B) and 11 show the output voltage characteristics of the above-described oil deterioration detector of the present invention. FIG. 10(A) is the output voltage characteristics when the oil is exchanged, while FIG. 10(B) is the output voltage characteristics when the oil is added. As apparent from FIGS. 10(A) and 10(B), it is found that the output voltage of the oil deterioration detector follows the variation of oil property (pH) with a time lag. Namely, it requires several minutes until the output voltage Vi of the oil deterioration detector reduces less than a warning threshold voltage Vt. It means that a warning lamp turns on erroneously during this time interval after the oil exchange or addition is over and the engine is started.

This invention eliminates this problem. An operation for this will be explained with reference to the flowchart of FIG. 11.

First of all, in a step S100, it is judged as to whether an oil temperature T is not less than a threshold temperature Tt (e.g. 80° C.). The step S100 is a sort of waiting step, which is needed for neglecting the slow change of the output voltage Vi when the oil temperature is low. If the judgement of the step S100 is YES, the output voltage Vi of the oil deterioration detector is read in (S102). Then, the moving average of the output voltage Vi is calculated (S104). Next, the rate-of-change G of the moving average of the output voltage Vi is calculated (S106). Subsequently, it is judged whether this rate-of-change G is not larger than a predetermined threshold value Gt (S108). If the judgement of the step S108 is NO, the procedure is again repeated from the step S100. On the contrary, if the judgement of the step S108 is YES, it is checked whether the output voltage Vi exceeds the warning threshold voltage Vt (S110). If the judgement of the step S110 is NO, the procedure is again repeated from the step S100. On the contrary, if the judgement of the step S110 is YES, the warning lamp is turned (S112).

With this control, the warning lamp is not turned on when the oil temperature T is low and the rate-of-change G of the output voltage Vi is large. Thus, it becomes possible to prevent the warning lamp from turning on erroneously. In the present invention, the oil temperature will be replaced by water temperature.

Hereinafter, an operation of the oil purification device 620, equipped with the oil deterioration detector, will be explained.

The oil, supplied from an oil pump (not shown), is introduced into the housing 628 through the oil passing holes 637b (refer to FIG. 16) opened on the flange portion 637a of the sleeve 637, as indicated by arrows. Then, the oil passes through the oil passing holes (not shown) opened on the reference electrodes 631 and the sensitive electrodes 632, and reaches the check valves 624 provided at the oil inlets 623 of the oil filter 622, contacting with the electrodes 631, 632 and the fixed layer 633 disposed therebetween. In this case, as the fixed layer 633 has the insulating porous structure, this fixed layer 633 does not obstruct electrochemical reactions occurring between the electrodes 631 and 632. Thus, the sensor amplifier 630b can generate an output voltage representing an accurate potential difference between electrodes 631 and 632. Meanwhile, after the oil has passed through the check valves 624, the oil further passes through the element 625 so that the oil is purified. Thereafter, the oil is supplied to lubrication portions of the engine through the outlet 627. The purification of the oil contaminated by non-soluble components is accomplished in this manner.

When the engine oil is green, the pH of the oil is approximately 7. In this case the output of the sensor amplifier 630b is less than the predetermined threshold value; therefore, the warning lamp 642 of the display unit 640 is turned off.

The amount of various oxides in the engine oil, such as SOx and NOx, increases with usage of the oil. Engine oil is usually deteriorated by these contaminated oxides, and the pH is lowered due to increase of hydrogen density. Therefore, when the oil is fairly deteriorated, the judging circuit 641 detects this condition by making a judgement as to whether the output voltage of the sensor amplifier 630b exceeds the threshold value. When the judging circuit 641 generates the output, the warning lamp is turned on to give warning to the driver.

By the way, the green-state oil contains moisture of 50 to 100 ppm, while the used oil contains moisture of 500 to 2000 ppm. The fixed layer 633 can collect this moisture; therefore the bath resistance between the electrodes is lowered and the output voltage is increased.

This embodiment brings the following effects:

(1) The input impedance Rin of the sensor amplifier 630b will fall within the range of existing devices, even if the value of this input impedance Rin is set to be sufficiently large compared with the bath resistance between the electrodes. Therefore, no countermeasure for preventing moisture in the air and leak current is necessary. Thus, cost will not increase;

(2) The output voltage becomes high compared with the conventional device, and the gradient of the output voltage is large; therefore, the S/N ratio is improved and the measurement accuracy is improved; and (3) As the oil deterioration condition is directly detected by checking the pH of the oil, it becomes possible to give an accurate warning to the driver.

Although this embodiment adopts the above-described hydrophilic filter for the fixed layer having the insulating and hydrophilic porous structure, this hydrophilic filter can be replaced by other materials, such as synthetic polymer series high-water-absorption resin, silica gel having fine holes, and foam ceramic.

This fixed layer can be coated directly on either or both of the reference electrode and the sensitive electrode, or can be fixed between these electrodes mechanically by means of bolts.

The fixed layer needs not to be brought into contact with the electrode. Even if a slight gap is provided between the fixed layer and the electrode so as to allow oil to enter therebetween, the similar effect will be obtained.

Although the reference electrode is made of lead, this embodiment will allow to use zinc, tin, indium, cadmium, magnesium, or their alloys, instead of lead. Furthermore, metals or their alloys having an oxide film layer thereon, such as nickel, titanium, niobium, tantalum, zirconium, aluminum can be used as the sensitive electrode, instead of stainless steel.

As this invention may be embodied in several forms without departing from the spirit of essential characteristics thereof, the present embodiments are therefore illustrative and not restrictive, since the scope of the invention is defined by the appending claims rather than by the description preceding them, and all changes that fall within meets and bounds of the claims, or equivalence of such meets and bounds are therefore intended to embraced by the claims.

What is claimed is:

1. An oil deterioration detector for detecting deterioration of an oil, comprising:

a sensitive electrode having an electrical potential that varies in correspondence with a pH level of the oil;

a reference electrode associated with said sensitive electrode;

an electrically conductive housing accommodating said sensitive electrode, said reference electrode, and the oil;

a potential difference detector for detecting oil deterioration by detecting a potential difference between said sensitive electrode and said reference electrode, wherein one of said sensitive electrode and said reference electrode has a reference electrical potential equal to an electrical potential of said electrically conductive housing, wherein said electrically conductive housing is a metallic oil device for circulating oil in an automobile, wherein one of said reference electrode and said sensitive electrode is integrally formed with and comprises a part of said metallic oil device, and the other of said reference electrode and said sensitive electrode is electrically insulated from said one of said reference electrode and said sensitive electrode and said metallic oil device.

2. An oil deterioration detector in accordance with claim 1, wherein said potential difference detector includes an amplifier for amplifying said potential difference between said reference electrode and said sensitive electrode, wherein said amplifier has an input connected to receive a reference value equal to said reference electrical potential.

3. An oil deterioration detector in accordance with claim 2, wherein said reference electrical potential is a grounded potential.

4. An oil deterioration detector in accordance with claim 1, wherein an insulating member is disposed between said reference electrode and said sensitive electrode.

5. An oil deterioration detector in accordance with claim 1, wherein at least at least one of said reference electrode and said sensitive electrode serves as a heat-dissipating radiator.

6. An oil deterioration detector in accordance with claim 1, wherein said reference electrode is plated with a Pb series metal.

7. An oil deterioration detector in accordance with claim 1, wherein said sensitive electrode is made from an electrically conductive material sheathed by an insulating film layer.

8. An oil deterioration detector in accordance with claim 1, wherein said reference electrode is plated with a Pb series metal, and said sensitive electrode is made from an electrically conductive material sheathed by an insulating film layer.

9. An oil deterioration detector in accordance with claim 1, wherein said electrically conductive housing is an oil cooler interposed along an oil passage between an oil filter and an engine in the automobile, wherein said reference electrode and said sensitive electrode are provided in said oil cooler.

10. An oil deterioration detector in accordance with claim 9, wherein one of said reference electrode and said sensitive electrode comprises a radiator member of said oil cooler.

11. An oil deterioration detector in accordance with claim 9, wherein at least one of said reference electrode and said sensitive electrode has a disk-shaped configuration having an oil passage hole for allowing oil to flow therethrough along an oil passage in the oil cooler.

12. An oil deterioration detector in accordance with claim 10, wherein said at least one of said reference electrode and said sensitive electrode has a disk-shaped configuration having an oil passage hole for allowing oil to flow therethrough along an oil passage in the oil cooler.

13. An oil deterioration detector in accordance with claim 11, wherein an insulating film layer is interposed between said reference electrode and said sensitive electrode.

14. An oil deterioration detector in accordance with claim 9, wherein said sensitive electrode is a cylindrical radiator member including an outer peripheral portion having a first diameter, an inner peripheral portion having a second diameter, and a disk-shaped portion extending radially so as to interconnect said outer peripheral portion and said inner peripheral portion.

15. An oil deterioration detector in accordance with claim 14, wherein said reference electrode is a metallic disk, and an insulating member is interposed between said metallic disk and said outer peripheral portion of said cylindrical radiator.

16. An oil deterioration detector in accordance with claim 15, wherein said metallic disk has a plurality of oil passage holes for allowing oil to flow along the oil passage in the oil cooler.

17. An oil deterioration detector in accordance with claim 16, wherein said sensitive electrode comprises a plurality of cylindrical radiators spaced apart along an axial direction of said oil cooler, wherein said metallic disk is interposed between adjacent said cylindrical radiators, wherein said oil cooler has an oil chamber at least partially defined by said plurality of cylindrical radiators.

18. An oil deterioration detector in accordance with claim 17, wherein said metallic disk is electrically grounded through a metallic body of said oil cooler.

19. An oil deterioration detector in accordance with claim 17, further including an electrically conductive cable connecting said outer peripheral portions of said plurality of cylindrical radiators, wherein an end of said cable is connected to said potential difference detector.

* * * * *